United States Patent

Rolf et al.

[11] 4,225,489
[45] Sep. 30, 1980

[54] HETEROCYCLIC AZO DYES AND PIGMENTS CONTAINING 4-QUINAZOLINONE MOIETIES

[75] Inventors: Meinhard Rolf; Rütger Neeff; Walter Müller, all of Leverkusen, Fed. Rep. of Germany

[73] Assignee: Bayer Aktiengesellschaft, Leverkusen, Fed. Rep. of Germany

[21] Appl. No.: 837,404

[22] Filed: Sep. 28, 1977

[30] Foreign Application Priority Data

Sep. 30, 1976 [DE] Fed. Rep. of Germany ....... 2644265

[51] Int. Cl.$^2$ ............... C09B 29/36; C09B 33/12; D06P 1/52; C09D 11/16
[52] U.S. Cl. ............................. 260/154; 106/23; 106/288 Q; 106/300; 106/300 Q; 106/308 N; 106/309; 260/208; 427/407.1; 428/411; 428/413; 428/480; 428/500; 428/538; 544/245; 544/284; 544/287
[58] Field of Search ........... 260/154; 544/245, 284, 544/287

[56] References Cited

U.S. PATENT DOCUMENTS

| | | | |
|---|---|---|---|
| 1,032,734 | 7/1912 | Bogert | 260/154 |
| 3,382,228 | 5/1968 | Ferrari et al. | 260/158 |
| 3,923,774 | 12/1975 | Dimroth | 260/154 |

FOREIGN PATENT DOCUMENTS

| | | | |
|---|---|---|---|
| 2245093 | 3/1974 | Fed. Rep. of Germany | 260/154 |
| 48-30655 | 9/1973 | Japan | 544/284 |

Primary Examiner—Floyd D. Higel
Attorney, Agent, or Firm—Sprung, Felfe, Horn, Lynch & Kramer

[57] ABSTRACT

Heterocyclic compounds of the formula

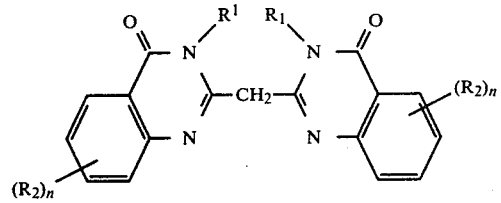

wherein
 $R_1$ denotes hydrogen or $C_1$–$C_4$-alkyl, or the two $R_1$s conjointly denote CO,
 $R_2$ denotes a substituent and
 n denotes 0, 1, 2, 3 or 4 are suitable as coupling components for azo dyestuffs and especially for azo pigments of the formula

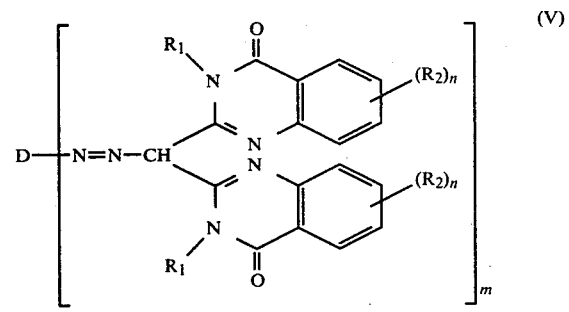

wherein
 D denotes the radical of an aromatic or heteroaromatic amine which is free from sulphonic acid groups and
 m denotes an integer, preferably 1 or 2, and $R_1$, $R_2$ and n have the abovementioned meaning.

4 Claims, No Drawings

HETEROCYCLIC AZO DYES AND PIGMENTS CONTAINING 4-QUINAZOLINONE MOIETIES

The invention relates to heterocyclic compounds of the formula

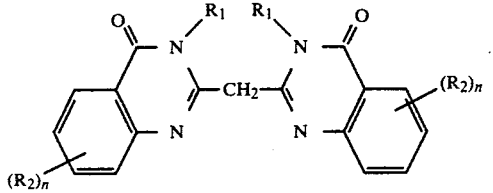

processes for their preparation, their use as coupling components for azo dyestuffs and the azo pigments prepared therefrom.

In the formula I
$R_1$ denotes hydrogen or $C_1$-$C_4$-alkyl, especially methyl, or the two $R_1$s conjointly denote CO,
$R_2$ denotes a substituent and n denotes 0, 1, 2, 3 or 4.

Examples of suitable substituents $R_2$ are halogen, such as chlorine and bromine, $C_1$-$C_4$-alkyl, $C_1$-$C_4$-alkoxy, nitro, trifluoromethyl, cyano, optionally substituted carboxamide and sulphonamide, acylamino or arylamino.

Possible substituents of the carboxamide and sulphonamide groups are $C_1$-$C_4$-alkyl, and phenyl and benzyl which are optionally substituted by $C_1$-$C_4$-alkyl, $C_1$-$C_4$-alkoxy, fluorine, chlorine, bromine or nitro. Acyl groups which may be mentioned are, in particular, $C_1$-$C_4$-alkylcarbonyl and benzoyl which is optionally substituted in the benzene nucleus by chlorine, $C_1$-$C_4$-alkyl, $C_1$-$C_4$-alkoxy or nitro. Arylamino is, in particular, phenylamino which is optionally substituted by $C_1$-$C_4$-alkyl, $C_1$-$C_4$-alkoxy, fluorine, chlorine, bromine or nitro.

The compounds of the formula I are obtained by reacting functional derivatives of malonic acid with anthranilic acid amides of the formula

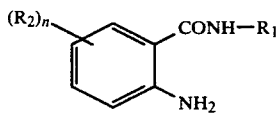

wherein
$R_1$, $R_2$ and n have the abovementioned meaning.

The malonic acid derivative and anthranilic acid amide are reacted in a molar ratio of 1:2 and, in general, the anthranilic acid amide is employed in a 0.1 to 10-fold excess. The reaction is reacted at 120° to 220° C., in bulk or in an inert organic solvent, such as o-dichlorobenzene, 1,2,4-trichlorobenzene, ethylene glycol dimethyl ether, ethylene glycol diethyl ether, xylene or nitrobenzene, optionally in the presence of catalytic amounts (0.001 to 0.1 mol per mol of malonic acid derivative) of organic bases, such as pyridine, quinoline, triethylamine, N,N-dimethylaniline or diazabicyclooctane.

Malonic acid derivatives which can be used are, in particular, the malonic acid halides, above all malonic acid dichloride, the malonic acid dialkyl esters, above all the dimethyl ester and diethyl ester, the malonic acid iminoalkyl esters, especially the dimethyl ester and diethyl ester, and malodinitrile.

The anthranilic acid amides of the formula II are obtained by reacting the corresponding isatoic anhydrides of the formula

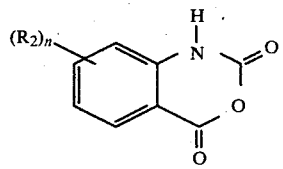

wherein
$R_2$ and n have the abovementioned meaning, with amines of the formula $$R_1-NH_2 \quad (IV)$$

wherein
$R_1$ has the abovementioned meaning.

The compounds of the formula I are pale yellow compounds which are sparingly soluble in organic solvents and have high melting points. They are suitable as coupling components for the preparation of azo dyestuffs and in particular for the preparation of azo pigments.

The compound in which $R_1$ denotes hydrogen and a n denotes O is particularly preferred.

The invention therefore also relates to azo pigments of the formula

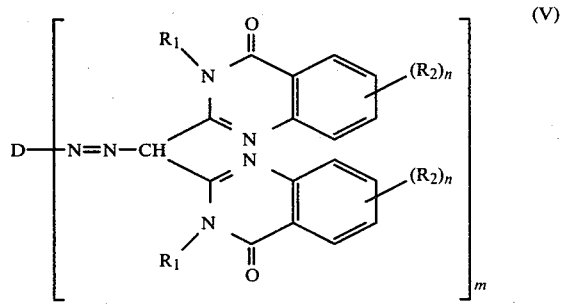

wherein
D denotes the radical of an aromatic or heteroaromatic amine which is free from sulphonic acid groups and
m denotes an integer, preferably 1 or 2, and
$R_1$, $R_2$ and n have the abovementioned meaning.

Examples of suitable diazo components are aniline, 2-methylaniline, 2,4-dimethylaniline, 2-nitraniline, 3-nitraniline, 4-nitraniline, 2,4-dinitraniline, 2-chloro-4-nitraniline, 4-chloro-2-nitraniline, 2-chloro-5-nitraniline, 2-nitro-4-methylaniline, 2-methyl-4-nitraniline, 2-methyl-5-nitraniline, 4-methoxy-2-nitraniline, 2-cyano-4-nitraniline, 2-bromo-4-nitraniline, 2-nitro-4-methylsulphonylaniline, 2-nitro-4-ethylsulphonylaniline, 2-chloroaniline, 4-chloroaniline, 2,4-dichloroaniline, 2,5-dichloroaniline, 2,6-dichloroaniline, 3,4-dichloroaniline, 3,5-dichloroaniline, 2,4,5-trichloroaniline, 2,4,6-trichloroaniline, 2-cyano-5-chloroaniline, 2-methyl-4-chloroaniline, 2-methyl-5-chloroaniline, 2,4-dichloro-5-ethylaniline, 2,5-dichloro-4-methylaniline, 2-chloro-4-methylsulphonylaniline, 2-cyano-5-chloroaniline, 2,4-dichloro-5-methoxyaniline, 2-chloro-5-trifluoromethylaniline, 4-chloro-2-trifluoromethylaniline, 3,5-bis-trifluoromethylaniline, 2,4-dimethoxyaniline, 2,5-dimethoxyaniline, 2,5-diethoxyaniline, 2,4-dimethoxy-5-chloroaniline, 2,5-dimethoxy-4-chloroaniline, 2-methoxy-5-methylaniline, 4-methoxy-2-methylaniline, 2-methoxy-5-methyl-4-chloroaniline, 2-methoxy-4-nitraniline, 4-methoxy-2-nitraniline, 2-methoxy-5-nitraniline, 2,5-dimethoxy-4-nitraniline, 2-methoxy-5-methyl-4-nitraniline, 2-methoxy-5-chloro-4-nitraniline, 2-methoxy-5-ethylsulphonylaniline, 2-methoxy-5-phenylsulphonylaniline, 2-methoxy-5-benzylsulphonylaniline, 2-methoxy-4-chloroaniline, 2-ethoxy-4-chloroaniline, 2-methoxy-5-chloroaniline, 2-ethoxy-5-chloroaniline, 2-methoxy-4,5-dichloroaniline, 2-amino-5-chlorodiphenyl ether, 2-amino-4,4'-dichlorodiphenyl ether, 2-amino-4,6-dichlorodiphenyl ether, 4-amino-5-methoxybenzenesulphonic acid 4-nitrophenyl ester, 5-acetylamino-2-nitraniline, 5-acetylamino-2-chloro-5-methylaniline, 4-acetylamino-2,5-dichloroaniline, 5-acetylamino-2,4-dichloroaniline, 4-benzoylamino-2-methyl-5-methoxyaniline, 5-benzoylamino-2-chloroaniline, 4-benzoylamino-2-chloro-5-methoxyaniline, 2-aminobenzoic acid methyl ester, 2-aminobenzoic acid ethyl ester, 2-aminobenzoic acid isobutyl ester, 4-chloro-2-amino-benzoic acid methyl ester, 5-chloro-2-aminobenzoic acid methyl ester, 6-chloro-2-amino-benzoic acid methyl ester, 3,5-dichloro-2-aminobenzoic acid methyl ester, 4,6-dichloro-2-aminobenzoic acid methyl ester, 5-bromo-2-aminobenzoic acid methyl ester, 4-nitro-2-aminobenzoic acid methyl ester, 5-nitro-2-aminobenzoic acid methyl ester, 4-methyl-2-aminobenzoic acid methyl ester, 5-methyl-2-aminobenzoic acid methyl ester, 6-methyl-2-aminobenzoic acid methyl ester, 4-trifluoromethyl-2-aminobenzoic acid methyl ester, 4-methoxy-2-aminobenzoic acid methyl ester, 4-methoxy-3-aminobenzoic acid phenyl ester, 4-carbamoyl-2-aminobenzoic acid methyl ester, 4-acetylamino-2-aminobenzoic acid methyl ester, 4-benzoylamino-2-aminobenzoic acid methyl ester, 4-(2,5-dichlorobenzoylamino)-2-aminobenzoic acid methyl ester, 4-sulphamoyl-2-aminobenzoic acid methyl ester, 2-aminonaphthalene-3-carboxylic acid methyl ester, 4-methyl-3-aminobenzoic acid methyl ester, 1-aminobenzene-2,5-dicarboxylic acid dimethyl ester, 1-aminobenzene-3,5-dicarboxylic acid dimethyl ester, 2-aminobenzoic acid amide, 4-aminobenzoic acid amide, 4-chloro-3-aminobenzoic acid amide, 4,6-dichloro-3-aminobenzoic acid amide, 3-amino-4-methoxy-benzoic acid amide, 3-amino-4-methoxybenzoic acid phenylamide, 3-amino-4-methylbenzoic acid methylamide, 3-amino-4-methylbenzoic acid (2,4-dimethylphenyl)-amide, 1-aminobenzene-3,5-dicarboxylic acid diamide, 3-amino-4-methylbenzoic acid (2,5-dichlorophenyl)-amide, 3-amino-4-methoxycarbonylbenzoic acid amide, 3-amino-4-methoxycarbonylbenzoic acid phenylamide, 3-amino-4-methoxycarbonylbenzoic acid (2,5-dichlorophenyl)-amide, 3-amino-4-methoxybenzenesulphonic acid methylamide, 3-amino-4-methoxybenzenesulphonic acid diethylamide, 2,5-dimethoxy-4-aminobenzenesulphonic acid methylamide, 2-methyl-5-methoxy-4-aminobenzenesulphonic acid methylamide, 3-amino-4-methylbenzenesulphonic acid phenylamide, 4-amino-2,5-dimethoxybenzenesulphonic acid methylamide, 4-amino-2-methyl-5-methoxybenzenesulphonic acid methylamide, 2-chloro-1-aminonaphthalene, 1-amino-2-methoxynaphthalene, 1-amino-4-nitronaphthalene, 2-amino-5-nitronaphthalene, 2-aminothiazole, 2-amino-4-methylthiazole, 2-amino-5-chlorothiazole, 2-amino-5-nitrothiazole, 2-amino-4-methylthiazole-5-carboxylic acid methyl ester, 2-amino-4-methylthiazole-5-carboxylic acid dimethylamide, 2-aminobenathiazole, 2-amino-6-methylbenzthiazole, 2-amino-5-methoxybenzthiazole, 2-amino-6-methoxybenzthiazole, 2-amino-6-chlorobenzthiazole, 2-amino-6-methylsulphonylbenzthiazole, 6-methyl-2-(4-aminophenyl)-benzthiazole, 5-amino-3-phenyl-1,2,4-thiadiazole, 2-amino-4-methylcarbostyril, 6-amino-4-methyl-2-chlorocarbostyril, 3-amino-4-methoxybenzoxazole, 6-amino-2,4-dihydroxyquinazoline, 1-aminoanthraquinone, 2-aminoanthraquinone, 1-amino-2-chloroanthraquinone, 1-amino-4-chloroanthraquinone, 1-amino-5-chloroanthraquinone, 1-amino-6-chloroanthraquinone, 1-amino-6(7)-chloroanthraquinone (mixture), 1-amino-5,8-dichloroanthraquinone, 1-amino-2-bromoanthraquinone, 1-amino-2,4-dibromoanthraquinone, 1-amino-6,7-dichloroanthraquinone, 1-amino-6-fluoroanthraquinone, 1-amino-7-fluoroanthraquinone, 1-amino-6,7-difluoroanthraquinone, 2-amino-1-chloroanthraquinone, 2-amino-3-chloroanthraquinone, 2-amino-3-bromoanthraquinone, 1-amino-4-nitroanthraquinone, 1-amino-5-nitroanthraquinone, 1-amino-2-methylanthraquinone, 1-amino-2-methyl-4-chloroanthraquinone, 1-amino-2-methyl-4-bromoanthraquinone, 1-aminoanthraquinone-2-carboxylic acid, 1-aminoanthraquinone-2-carboxylic acid amide, 1-aminoanthraquinone-2-carboxylic acid methyl ester, 1-amino-4-nitroanthraquinone-2-carboxylic acid, 1-amino-2-acetylanthraquinone, 1-amino-5-benzoylaminoanthraquinone, 1-amino-4-benzoylaminoanthraquinone, 1-amino-4-hydroxyanthraquinone, 1-amino-5-hydroxyanthraquinone, 1-amino-4-methoxyanthraquinone, 1-amino-2-methoxy-4-hydroxyanthraquinone, 1-amino-4-methylaminoanthraquinone, 1-amino-4-cyclohexylaminoanthraquinone, 1-amino-4-anilinoanthraquinone, 1-amino-6-methylmercaptoanthraquinone, 2-phenyl-6-amino-4,5-phthaloylbenzimidazole, 6-chloro-2-amino-3,4-phthaloylacridone, 7-chloro-2-amino-3,4-phthaloylacridone, 5-chloro-8-amino-3,4-phthaloylacridone, 4-aminoanthrapyridone, 5-aminoanthrapyridone, 1,5-diaminoanthraquinone, 1,4-diaminoanthraquinone, 1,8-diaminoanthraquinone, 2,6-diaminoanthraquinone, 1,5-diamino-4-chloroanthraquinone, 1,4-diamino-5-nitroanthraquinone, 1,5-diamino-2,4,6,8-tetrabromoanthraquinone, 1,5-diamino-4,8-dihydroxyanthraquinone, 1,8-diamino-4,5-dihydroxyanthraquinone, 4,4'-diamino-1,1'-dianthrimide, 4,4'-diaminobiphenyl, 4,4'-diamino-3,3'-dimethoxybiphenyl, 4,4'-diamino-3,3'-diethoxybiphenyl, 4,4'-diamino-2,2'-dichlorobiphenyl, 4,4'-diamino-3,3'-dichlorobiphenyl, 4,4'-diamino-2,2', 5,5'-tetrachlorobiphenyl, 4,4'-diamino-2-nitrobiphenyl, 4,4'-diamino-3-methylbiphenyl, 4,4'-diamino-2,2'-dimethylbiphenyl, 4,4'-diamino-3,3'-dimethylbiphenyl, 4,4'-diamino-3,3'-dimethoxy-6,6-dichlorobiphenyl, 1-amino-8-benzoylaminoanthraquinone and 1-amino-2-bromo-4-(4-methylphenylsulphonylamino)-anthraquinone.

Preferred diazo components are those of the benzene and anthraquinone series.

Dyestuffs of the formula

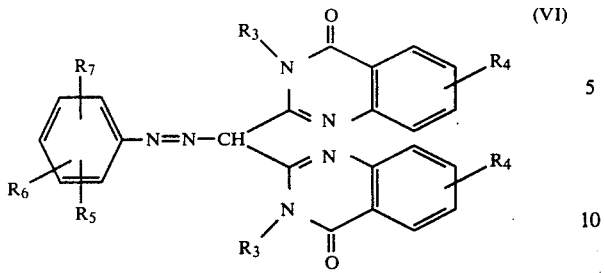

(VI)

wherein
- $R_3$ denotes hydrogen or methyl,
- $R_4$ denotes hydrogen, $C_1$-$C_4$-alkyl, $C_1$-$C_4$-alkoxy, fluorine, chlorine, bromine, nitro, $C_1$-$C_4$-alkylcarbonylamino or $C_1$-$C_4$-alkylsulphonylamino,
- $R_5$ denotes hydrogen, halogen, such as fluorine, chlorine and bromine, $C_1$-$C_4$-alkyl, $C_1$-$C_4$-alkoxy, nitro, cyano, $C_1$-$C_4$-alkylsulphonyl, trifluoromethyl, $C_1$-$C_4$-alkylcarbonylamino, benzoylamino which is optionally substituted by $C_1$-$C_4$-alkyl, $C_1$-$C_4$-alkoxy, fluorine, chlorine, bromine or nitro, $C_1$-$C_4$-alkoxycarbonyl, or carboxamide or sulphonamide which are optionally monosubstituted or disubstituted by $C_1$-$C_4$-alkyl, phenyl or benzyl, it being possible for phenyl and benzyl to be further substituted by $C_1$-$C_4$-alkyl, $C_1$-$C_4$-alkoxy, fluorine, chlorine, bromine and nitro,
- $R_6$ denotes hydrogen, halogen, such as fluorine, chlorine and bromine, $C_1$-$C_4$-alkyl, cyano, $C_1$-$C_4$-alkoxy, nitro or trifluoromethyl and
- $R_7$ denotes hydrogen, chlorine, $C_1$-$C_4$-alkyl or $C_1$-$C_4$-alkoxy, are particularly preferred.

Further preferred dyestuffs correspond to the formula

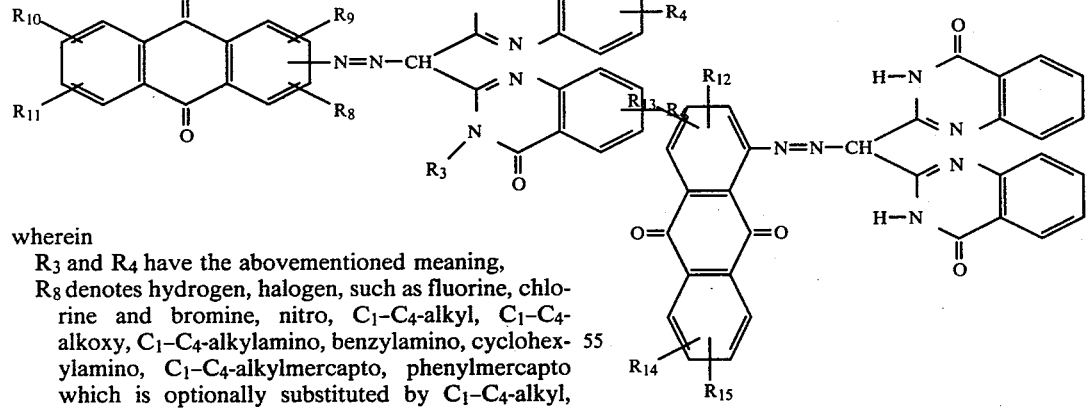

(VI)

wherein
- $R_3$ and $R_4$ have the abovementioned meaning,
- $R_8$ denotes hydrogen, halogen, such as fluorine, chlorine and bromine, nitro, $C_1$-$C_4$-alkyl, $C_1$-$C_4$-alkoxy, $C_1$-$C_4$-alkylamino, benzylamino, cyclohexylamino, $C_1$-$C_4$-alkylmercapto, phenylmercapto which is optionally substituted by $C_1$-$C_4$-alkyl, $C_1$-$C_4$-alkoxy, fluorine, chlorine, bromine or nitro, $C_1$-$C_4$-alkylcarbonyl, $C_1$-$C_4$-alkoxycarbonyl, phenylamino which is optionally substituted by $C_1$-$C_4$-alkyl, $C_1$-$C_4$-alkoxy, chlorine or nitro, carboxamide which is optionally monosubstituted or disubstituted by $C_1$-$C_4$-alkyl, benzyl or phenyl, it being possible for phenyl to be substituted by $C_1$-$C_4$-alkyl, $C_1$-$C_4$-alkoxy, fluorine, chlorine, bromine or nitro, carboxyl, hydroxyl, $C_1$-$C_4$-alkylcarbonylamino or benzoylamino which is optionally substituted by $C_1$-$C_4$-alkyl, $C_1$-$C_4$-alkoxy, chlorine, bromine or nitro, $C_1$-$C_4$-alkylsulphonylamino or phenylsulphonylamino which is optionally substituted by $C_1$-$C_4$-alkyl, $C_1$-$C_4$-alkoxy, fluorine, chlorine, bromine or nitro,
- $R_9$ denotes hydrogen, chlorine or hydroxyl,
- $R_{10}$ denotes hydrogen, halogen, such as fluorine, chlorine or bromine, nitro, $C_1$-$C_4$-alkyl, $C_1$-$C_4$-alkoxy, $C_1$-$C_4$-alkylamino, $C_1$-$C_4$-alkylmercapto, phenylmercapto which is optionally substituted by $C_1$-$C_4$-alkyl, $C_1$-$C_4$-alkoxy, fluorine, chlorine, bromine or nitro, $C_1$-$C_4$-alkoxycarbonyl, $C_1$-$C_4$-alkylcarbonyl, benzylamino, cyclohexylamino, phenylamino which is optionally substituted by $C_1$-$C_4$-alkyl, $C_1$-$C_4$-alkoxy, chlorine, bromine or nitro, carboxyl, hydroxyl, carboxamide which is optionally monosubstituted or disubstituted by $C_1$-$C_4$-alkyl, benzyl or phenyl, it being possible for phenyl to be substituted by $C_1$-$C_4$-alkyl, $C_1$-$C_4$-alkoxy, fluorine, chlorine, bromine or nitro, $C_1$-$C_4$-alkyl, carbonylamino, benzoylamino which is optionally substituted by $C_1$-$C_4$-alkyl, $C_1$-$C_4$-alkoxy, chlorine, bromine or nitro, $C_1$-$C_4$-alkylsulphonylamino or phenylsulphonylamino which is optionally substituted by $C_1$-$C_4$-alkyl, $C_1$-$C_4$-alkoxy, fluorine, chlorine, bromine or nitro and
- $R_{11}$ denotes hydrogen, halogen, such as fluorine, chlorine and bromine, or hydroxyl.

Pigments of the formula (VIII)

wherein
- $R_{12}$, $R_{13}$, $R_{14}$ and $R_{15}$ denote hydrogen, chlorine, bromine, carboxyl, $C_1$-$C_4$-alkoxycarbonyl, carboxamide, $C_1$-$C_4$-alkylcarbonylamino, benzoylamino which is optionally substituted by 1 or 2 nitro or 1 to 5 chlorine or bromine, $C_1$-$C_4$-alkylsulphonylamino or phenylsulphonylamino which is optionally substituted by methyl, methoxy or chlorine, are very particularly preferred.

The azo pigments V are prepared by a coupling reaction of diazotised aromatic amines of the formula $$D-NH_2 \qquad (IX)$$

wherein
D has the abovementioned meaning,
with the heterocyclic compounds I.

Several processes can be employed for the coupling reactions:

(1) An aqueous or alkaline aqueous suspension or solution of the coupling component is added to the acid aqueous diazonium salt solution. The mixture is stirred until the reaction has ended and the dyestuff is purified by heating in an organic solvent, such as n-butanol, toluene, chlorobenzene, pyridine, nitrobenzene, o-dichlorobenzene, 1,2,4-trichlorobenzene, tetramethylenesulphone, dimethylformamide, N-methylpyrrolidone, ethylene glycol dimethyl ether or ethylene glycol diethyl ether.

(2) The diazo component VIII is diazotised in an organic solvent, such as dimethylformamide, dimethylacetamide, dimethylsulphoxide, tetramethylenesulphone, tetraphenylurea, N-methylpyrrolidone, nitrobenzene, o-dichlorobenzene, 1,2,4-trichlorobenzene, ethylene glycol dimethyl ether, ethylene glycol diethyl ether or acetic acid, in the presence of an acid, such as sulphuric acid, phosphoric acid, benzenesulphonic acid, ethanesulphonic acid, p-toluenesulphonic acid, naphthalene-2,6-disulphonic acid, formic acid, acetic acid, dichloroacetic acid, 2,4-dichlorobenzoic acid, oxalic acid, succinic acid, maleic acid, tartaric acid or terephthalic acid, with organic nitrites, such as methyl nitrite, ethyl nitrite or isoamyl nitrite, or, advantageously, with nitrites of glycols and glycol derivatives, such as methoxyethyl nitrite or ethoxyethyl nitrite, or alkali metal nitrites, such as sodium nitrite. A suspension of the coupling component, appropriately in the same solvent, is then stirred in. After the coupling reaction has ended, the high product is purified in the coupling solution by raising the temperature to 90° to 200° C. and isolated by filtering off.

The second process can also be varied to the effect that the diazo component and coupling component in the organic solvent are initially introduced and the alkyl nitrite or alkali methane nitrite is added, so that the diazotisation and the coupling reaction take place at the same time. This process variant also is appropriately followed by a high temperature treatment in order to purify the pigment prepared in this way.

The pigments of the formula V are obtained in a form suitable for pigments or can be converted into the suitable form by after-treatment processes which are in themselves known, for example by dissolving or swelling in strong inorganic acids, such as sulphuric acid, and discharging onto ice. The state of fine division can also be achieved by grinding, with or without grinding aids, such as inorganic salts or sand, optionally in the presence of solvents, such as toluene, xylene, dichlorobenzene or N-methylpyrrolidone. The depth of colour and transparency of the pigment can be influenced by varying the after-treatment.

Because of their fastness to light and migration, the pigments of the formula V are suitable for very diverse pigment applications. The pigments according to the invention can be used for the preparation of systems with very fast pigmentation, such as mixtures with other substances, formulations, paints, printing inks, coloured paper and coloured macromolecular substances. A mixture with other substances can be understood, for example, as a mixture with inorganic white pigments, such as titanium dioxide (rutile), or with cement. Formulations are, for example, flush pastes with organic liquids or pastes or fine pastes with water, dispersing agents and, optionally, preservatives. The term paints represents, for example, lacquers which dry by physical means or by oxidation, stoving lacquers, reactive lacquers, two-component lacquers, latex paints for weather-resistant coatings and distempers. Printing inks are to be understood as those for printing paper, textiles and sheet metals. The macromolecular substances can be of natural origin, such as rubber, obtained by chemical modification, such as acetylcellulose, cellulose butyrate or viscose, or synthetically produced, such as polymers, polyaddition products and polycondensation products. Plastic compositions, such as polyvinyl chloride, polyvinyl acetate, polyvinyl propionate, polyolefines, for example polyethylene or polypropylene, polyesters, for example polyethylene terephthalate, polyamides, high molecular weight polyamides, polymers and copolymers of acrylates, methacrylates, acrylonitrile, acrylamide, butadiene and styrene as well as polyurethanes and polycarbonates may be mentioned. The substances pigmented with the products claimed can be in any desired form.

The pigments V according to the invention furthermore are outstandingly fast to water, fast to oil, fast to acid, fast to lime, fast to alkali, fast to solvents, fast to over-lacquering, fast to over-spraying, fast to sublimation, resistant to heat and resistant to vulcanising, give a very good colour yield and can be dispersed readily in plastic compositions.

EXAMPLE 1

19 g of malonic acid diethyl ester, 35 g of anthranilic acid amide and 5 g of pyridine are added to 80 g of o-dichlorobenzene. The mixture is heated under reflux to 150° to 160° C. for 2 hours and a mixture of water, ethanol and pyridine is then distilled off for 3 hours at 170° C. After cooling the residue to 50° C., the precipitate is filtered off, washed with o-dichlorobenzene and methanol and dried at 80° in vacuo. 30 g (80% of theory) of the compound of the formula

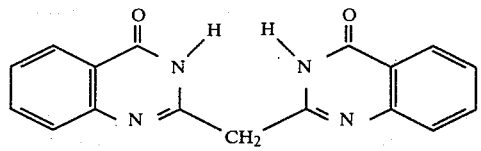

are obtained as a yellowish powder which does not melt on heating to 300° C. The composition is confirmed by elementary analysis: found (calculated): C: 67.4 (67.0), H: 4.3 (4.0), N: 18.7 (18.4).

The following compounds are prepared by the process indicated in Example 1 using substituted anthranilic acid amides in place of anthranilic acid amide and are purified by recrystallisation from dimethylformamide.

| Example | R₁  | R₃ | R₄      | R₅      | R₆ |
|---------|-----|----|---------|---------|-----|
| 2       | CH₃ | H  | H       | H       | H   |
| 3       | H   | Br | H       | H       | H   |
| 4       | H   | Cl | H       | H       | H   |
| 5       | H   | H  | Cl      | H       | H   |
| 6       | CH₃ | H  | H       | Cl      | H   |
| 7       | H   | H  | Cl      | H       | Cl  |
| 8       | H   | H  | NO₂     | H       | H   |
| 9       | CH₃ | H  | H       | NO₂     | H   |
| 10      | H   | H  | NHCOCH₃ | H       | H   |
| 11      | H   | H  | H       | NHCOCH₃ | H   |

The analytical values found for the individual products agree well with the calculated values and are not given separately here. All of the compounds are yellow powders which at 300° C. have not yet melted and which are insoluble or only sparingly soluble in the customary organic solvents.

EXAMPLE 12

(a) 35 g of 1-amino-5-benzoylaminoanthraquinone (87% pure) are dissolved in 180 g of sulphuric acid, whilst cooling with ice, and diazotised with 30 g of nitrosylsulphuric acid (42% strength in sulphuric acid). After diluting the mixture with 250 g of water, the excess nitrite is destroyed with amidosulphonic acid and a suspension of 30 g of the compound obtained according to Example 1 in 150 g of 20% strength aqueous potassium hydroxide solution is added in portions at 70° C. After 30 minutes the mixture is filtered hot and the material on the filter is washed with hot water until neutral. The product is filtered off and, in 300 ml of nitrobenzene, is freed from water at 130° C. by distillation.

In order to achieve a better pigment quality, the product is then heated briefly in nitrobenzene to 160° C. The mixture is allowed to cool to 100° C. and filtered and the product is washed with nitrobenzene and methanol and dried in vacuo at 80°. This gives 52 g (90% of theory) of the orange-coloured pigment of the formula

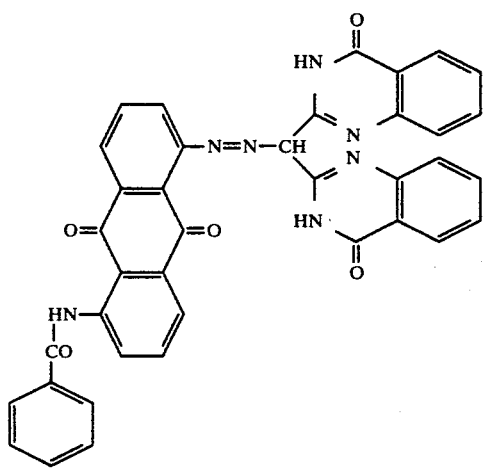

(b) 7 g of 1-amino-5-benzoylaminoanthraquinone (87% pure), 7.5 g of the compound obtained according to Example 1 and 5 g of dichloroacetic acid are added to 80 g of nitrobenzene. 3 g of isoamyl nitrite in 17 g of nitrobenzene are added dropwise at 70° C. The mixture is stirred for 3 hours at 70° C. and then heated briefly to 160° C. and the precipitate is filtered off and rinsed with hot nitrobenzene and methanol. After drying, 11 g (94% of theory) of the pigment indicated in Example 12a are obtained.

(c) 7 g of 1-amino-5-benzoylaminoanthraquinone (87% pure) are diazotised in 90 g of dimethylformamide with 14 g of nitrosylsulphuric acid. After destroying the excess nitrite with amidosulphonic acid, 7.5 g of the product obtained according to Example 1 are added and the mixture is stirred for 2 hours at 70° C. It is then heated briefly to 140° C. and the precipitate is filtered off at 80° C., rinsed with dimethylformamide and hot water and dried. 9 g (77% of theory) of the pigment indicated in Example 12a are obtained.

(d) 7 g of 1-amino-5-benzoylaminoanthraquinone (87% pure), 7.5 g of the product obtained according to Example 1 and 2 g of sodium nitrite are added to 120 g of nitrobenzene. 6 g of technical grade formic acid (85% strength) are added dropwise at 70° C. After stirring the mixture for one hour at 70° C., the temperature is raised to 150° C. for a short time, the mixture is filtered at 100° C. and the product is washed with hot nitrobenzene and methanol. After drying in vacuo, 10 g (86% of theory) of the pigment indicated in Example 12a are obtained.

EXAMPLE 13

4.1 g of 2-nitraniline in 90 g of dimethylformamide are diazotised at 5° C. with 9 g of nitrosylsulphuric acid (42% strength in sulphuric acid). A suspension of the product obtained according to Example 1 in 20 g of dimethylformamide is then added and the mixture is filtered after stirring for 2 hours at 5° C. After washing with dimethylformamide and hot water, the product is dried. 13 g (96% of theory) of the yellow pigment of the formula

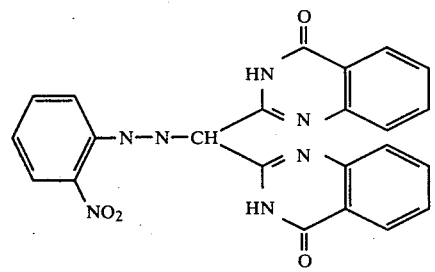

are obtained.

Using the diazo components listed in the table which follows in place of 2-nitraniline, corresponding azo pigments with the indicated colour shades are obtained by the process described in Example 13.

TABLE 1

| Examples | Diazo component        | Colour shade           |
|----------|------------------------|------------------------|
| 14       | aniline                | greenish-tinged yellow |
| 15       | 2,4-dimethylaniline    | greenish-tinged yellow |
| 16       | 2-chloroaniline        | yellow                 |
| 17       | 3-amino-4-chlorobenzamide | yellow              |
| 18       | 3-nitroaniline         | greenish-tinged yellow |
| 19       | 2-nitro-4-chloroaniline | yellow                |

TABLE 1-continued

| Examples | Diazo component | Colour shade |
|---|---|---|
| 20 | 2-chloro-4-nitraniline | yellow |
| 21 | anthranilic acid amide | yellow |
| 22 | 3-trifluoromethylaniline | greenish-tinged yellow |
| 23 | 2-trifluoromethyl-4-chloroaniline | greenish-tinged yellow |
| 24 | 2-methoxyaniline | yellow |
| 25 | 4-methoxyaniline | yellow |
| 26 | 4-aminobenzoic acid methyl ester | yellow |
| 27 | 5-amino-isophthalic acid dimethyl ester | greenish-tinged yellow |
| 28 | 3,4-dicyanoaniline | yellow |
| 29 | 4-methoxy-4'-aminodiphenylamine | reddish-tinged yellow |
| 30 | 4-aminoazobenzene | reddish-tinged yellow |
| 31 | 3,3'-dichloro-4,4'-diaminobiphenyl | yellow |
| 32 | 3,3'-dimethoxy-4,4'-diaminobiphenyl | red |
| 33 | 4-(4-aminobenzoylamino)-aniline | yellow |
| 34 | 1-aminoanthraquinone | orange |
| 35 | 2-aminoanthraquinone | reddish-tinged yellow |
| 36 | 4-chloro-1-aminoanthraquinone | orange |
| 37 | 2-methyl-1-aminoanthraquinone | orange |
| 38 | 4-methoxy-1-aminoanthraquinone | red |
| 39 | 2-carboxy-1-aminoanthraquinone | orange |
| 40 | 2-aminothiazole | orange |
| 41 | 2-aminobenzthiazole | orange |

Further pigments which have the colour shades indicated in the table which follows are obtained by the process described in Example 13 when the diazo components indicated in the second column are used in place of 2-nitraniline and the coupling components indicated in the third column are used in place of the coupling component obtained according to Example 1.

TABLE 2

| Example | Diazo component | Coupling component | Colour shade |
|---|---|---|---|
| 42 | Anthranilic acid amide | Example 2 | yellow |
| 43 | 4-nitro-2-chloroaniline | Example 2 | yellow |
| 44 | 3-nitraniline | Example 5 | greenish-tinged yellow |
| 45 | 1-aminoanthraquinone | Example 6 | orange |
| 46 | 1-amino-5-nitro-anthraquinone | Example 2 | orange |
| 47 | 1-amino-4-chloro-anthraquinone | Example 10 | orange |
| 48 | 1-amino-5-benzoylamino-anthraquinone | Example 8 | orange |
| 49 | 1-amino-4-methoxy-anthraquinone | Example 8 | red |
| 50 | 2-aminobenzthiazole | Example 2 | orange |

EXAMPLE 51

(a) 8 g of the finely divided pigment obtained according to Example 12 are ground with a stoving lacquer consisting of 25 g of coconut oil alkyd resin (40% coconut oil), 10 g of melamine resin, 50 g of toluene and 7 g of glycol monomethyl ether on an automatic Hoover-Muller grinding machine. The mixture is applied to the substrate to be lacquer-coated and the lacquer is cured by stoving at 130° C. and orange lacquer coatings with very good fastness to over-lacquering and outstanding fastness to light and weathering are obtained.

Pigmented stoving lacquers with equal fastness properties are obtained when 15–25 g of the indicated alkyd resin or of an alkyd resin based on cottonseed oil, dehydrated castor oil, castor oil or synthetic fatty acids are used and, in place of the indicated amount of melamine resin, 10–15 g of the melamine resin mentioned or of a condensation product of formaldehyde and urea or benzoguanamine are employed.

(b) If, in place of the indicated amount of pigment, 1 to 10 g of a mixture of titanium dioxide (rutile type) with the pigment indicated in Example 51a are ground, in a ratio of 0.5–50:1, into the lacquer indicated in Example 51a, the same further processing gives lacquer coatings which have equal fastness properties and an orange colour shade which is shifted towards white as the titanium dioxide content increases.

EXAMPLE 52

6 g of the finely divided pigment according to Example 12 are ground into 100 g of a nitrocellulose lacquer which consists of 44 g of collodion cotton (of low viscosity, 35% strength, butanol-moist), 5 g of dibutyl phthalate, 40 g of ethyl acetate, 20 g of toluene, 4 g of n-butanol and 10 g of glycol monomethyl ether. After spreading and drying, orange-coloured lacquer coatings with outstanding fastness to light and over-lacquering are obtained. The use of nitro lacquers which have a nitrocellulose content of 10–15 g and a plasticiser content of 5–10 g and 70–85 g of a solvent mixture, in which aliphatic esters, such as ethyl acetate and butyl acetate, and aromatic compounds, such as toluene and xylene, and, in smaller proportions, aliphatic ethers, such as glycol ether, and alcohols, such as butanol, are preferably used, gives the same results. Plasticisers can be understood, for example, as phthalic acid esters, such as dioctyl phthalate and dibutyl phthalate, esters of phosphoric acid, and castor oil, on its own or in combination with oil-modified alkyd resins.

Lacquer coatings which have similar fastness properties are obtained when other spirit lacquers, Zapon lacquers and nitro lacquers which dry by physical means, air-drying oil lacquers, synthetic resin lacquers and nitro combination lacquers and oven-drying and air-drying epoxide resin lacquers, optionally in combination with urea resins, melamine resins, alkyd resins or phenolic resins, are used.

EXAMPLE 53

5 g of the pigment according to Example 12, which has been brought into a state of fine division, are ground in 100 g of a paraffin-free, drying unsaturated polyester resin in a porcelain ball mill. 10 g of styrene, 59% of melamine-formaldehyde resin and 1 g of a paste of 40 g of cyclohexanone peroxide and 60% of dibutyl phthalate are stirred well with the ground mixture and, finally, 4 g of dryer solution (10% strength cobalt naphthenate in test benzine) and 1 g of silicone oil solution (1% strength in xylene) are mixed in. The mixture is applied to primed wood and an orange-coloured lacquer coating which has a high gloss and is resistant to water and fast to weathering and has outstanding fastness to light is obtained.

If amine-curing epoxide resin lacquers with dipropylenediamine as the amino component are used in place of the reactive lacquer based on an unsaturated polyester resin, orange-coloured lacquer coatings with outstanding fastness to weathering and blooming are obtained.

EXAMPLE 54

100 g of a 65% strength solution of an aliphatic polyester, containing about 8% of free hydroxyl groups, in glycol monoethyl ether-acetate are ground with 5 g of the pigment obtained according to Example 12 and the mixture is then mixed well with 44 g of a 67% strength solution of the reaction product obtained from 1 mol of trimethylolpropane and 3 mols of toluylene diisocyanate. After application of the mixture and reaction of the components, orange-coloured polyurethane lacquer coatings which have a high gloss and outstanding fastness to blooming, light and weathering are obtained, with no impairment of the pot life.

Pigmentation of similar fastness is obtained when other two-component lacquers based on aromatic or aliphatic isocyanates and polyethers or polyesters containing hydroxyl groups are used and also with moisture-drying polyisocyanate lacquers which give polyurea lacquer coatings.

EXAMPLE 55

5 g of a fine paste obtained by kneading 50 g of the pigment obtained according to Example 12 with 15 g of an arylpolyglycol ether emulsifier and 35 g of water are mixed with 10 g of barytes, as the filler, 10 g of titanium dioxide (rutile type), as the white pigment, and 40 g of an aqueous latex paint, contain about 50% of polyvinyl acetate. The paint is spread and, after drying, orange-coloured paint coatings with very good fastness to lime and cement as well as outstanding fastness to weathering and light are obtained.

The fine paste obtained by kneading is likewise suitable for the pigmentation of clear polyvinyl acetate latex paints, for latex paints which contain copolymers of styrene and maleic acids as the binder and latex paints based on polyvinyl propionate, polymethacrylate or butadiene-styrene.

EXAMPLE 56

10 g of the pigment paste mentioned in Example 55 are mixed with a mixture of 5 g of chalk and 5 g of a 20% strength size solution. This gives an orange-coloured wallpaper paint, with which coatings with outstanding fastness to light are obtained. Other non-ionic emulsifiers, such as the reaction products of nonylphenol and ethylene oxide, or ionic wetting agents, such as the sodium salts of alkylarylsulphonic acids, for example of dinaphthylmethanedisulphonic acid, sodium salts of substituted sulpho-fatty acid esters and sodium salts of paraffinsulphonic acids in combination with alkylpolyglycol ethers can also be used to prepare the pigment paste.

EXAMPLE 57

A mixture of 65 g of polyvinyl chloride, 35 g of diisooctyl phthalate, 2 g of dibutyl-tin mercaptide, 0.5 g of titanium dioxide and 0.5 g of the pigment from Example 12 is coloured on a mixing mill at 165° C. This gives an intensely orange-coloured composition which can be used for the preparation of films or mouldings. The coloration is distinguished by outstanding fastness to light and very good fastness to plasticisers.

EXAMPLE 58

0.2 g of the pigment according to Example 12 is mixed with 100 g of polyethylene, polypropylene or polystyrene granules. The mixture can either be injection-moulded direct at 220° to 280° C. in an injection moulding machine or can be processed in an extruder to give coloured rods or can be processed on a mixing mill to give coloured hides. The rods or hides are optionally granulated and injection-moulded in an injection machine.

The orange-coloured mouldings have very good fastness to light and migration. In a similar manner, synthetic polyamides of caprolactam or adipic acid and hexamethylenediamine, or the condensation products of terephthalic acid and ethylene glycol, can be coloured at 280°-300° C., if appropriate under a nitrogen atmosphere.

EXAMPLE 59

1 g of the pigment according to Example 12, 10 g of titanium dioxide (rutile type) and 100 g of a copolymer which is based on acrylonitrile/butadiene/styrene and in powder form are mixed and coloured on a roll mill at 140°-180° C. An orange-coloured hide is obtained and this is granulated and injection-moulded in an injection moulding machine at 200°-250° C. Orange-coloured mouldings which have very good fastness to light and migration as well as excellent resistance to heat are obtained.

Plastics based on cellulose acetate or cellulose butyrate and mixtures thereof are coloured with similar fastness properties in a similar manner, but at temperatures of 180°-220° C. and without addition of titanium dioxide.

EXAMPLE 60

0.2 g of the pigment according to Example 12, in the finely divided form, are mixed with 100 g of a plastic based on polycarbonate in an extruder or in a kneading screw at 250°-280° C. and the mixture is processed to give granules. Orange-coloured transparent granules with outstanding fastness to light and resistance to heat are obtained.

EXAMPLE 61

90 g of a slightly branched polypropylene glycol with a molecular weight of 2,500 and a hydroxyl number of 56, 0.25 g of endoethylenepiperazine, 0.3 g of tin-(II) octoate, 1.0 g of a polyether siloxane, 3.5 g of water and 12.0 g of a ground mixture of 10 g of the pigment according to Example 12 in 50 g of the indicated polypropylene glycol are mixed well together and then intimately mixed with 45 g of toluylene diisocyanate (80% of the 2,4 isomer and 20% of the 2,6 isomer) and the resulting mixture is poured into a mould. The mixture becomes turbid after 6 seconds and a foam is formed. An intensely orange-coloured soft polyurethane foam has formed after 70 seconds and the pigmentation of this foam displays outstanding fastness to light.

EXAMPLE 62

90 g of a slightly branched polyester which is obtained from adipic acid, diethylene glycol and trimethylolpropane and has a molecular weight of 2,000 and a hydroxyl number of 60 are mixed with the following components: 1.2 g of dimethylbenzylamine, 2.5 g of sodium castor oil-sulphate, 2.0 g of an oxethylated, benzylated hydroxydiphenyl, 1.75 g of water and 12 g of a paste prepared by grinding 10 g of the pigment according to Example 12 in 50 g of the polyester indicated above. After mixing, 40 g of toluylene diisocyanate (65% of the 2,4 isomer and 35% of the 2,6 isomer)

are stirred in, whilst stirring, and the mixture is poured into a mould and foamed. After 60 seconds an orange-coloured, soft polyurethane foam has formed, the coloration of which is distinguished by very good fastness to light.

EXAMPLE 63

Orange-coloured offset prints of high billiance and depth of colour and with very good fastness to light and lacquering are obtained using a printing ink prepared by grinding 35 g of the pigment according to Example 12 and 65 g of linseed oil and adding 1 g of a sicoativ (Co naphthenate, 50% strength in test benzine). The use of this printing ink in letterpress printing, collotype printing, lithographic printing or die stamping leads to orange-coloured prints with similar fastness properties. If the pigment is used to colour tin printing inks or gravure printing inks of low viscosity or printing inks, orange-coloured prints with similar fastness properties are obtained.

EXAMPLE 64

A printing paste is prepared from 10 g of the pigment fine paste indicated in Example 55, 100 g of 3% strength tragacanth, 100 g of an aqueous 50% strength egg albumin solution and 25 g of a non-ionic wetting agent. A textile fibre fabric is printed and steamed at 100° C. and an orange-coloured print which is distinguished by outstanding fastness properties, especially fastness to light, is obtained. Other binders which can be used for fixing the pigment on the fibre, for example those based on synthetic resin, British gum or cellulose glycollate, can be used in the printing batch in place of the tragacanth and egg albumin.

EXAMPLE 65

A mixture of 100 g of light crepe, 2.6 g of sulphur, 1 g of stearic acid, 1 g of mercaptobenzthiazole, 0.2 g of hexamethylenetetramine, 5 g of zinc oxide, 60 g of chalk and 2 g of titanium dioxide (anatase type) is coloured, on a mixing mill, at 50° C. with 2 g of the pigment obtained according to Example 12 and then vulcanised at 140° C. for 12 minutes. An orange-coloured vulcanised product with very good fastness to light is obtained.

EXAMPLE 66

22.5 l of an aqueous, approximately 9% strength viscose solution are added to 100 g of a 20% strength aqueous paste of the pigment according to Example 12, prepared, for example, by dissolving the dyestuff in 96% strength sulphuric acid, discharging the mixture onto ice, filtering and washing the product with water until neutral, in a stirred apparatus. The coloured mass is stirred for 15 minutes, the air is then removed and the composition is subjected to a spinning process and desulphurising process.

Orange-coloured filaments or films with very good fastness to light are obtained.

EXAMPLE 67

10 kg parts of a paper pulp containing 4 g of cellulose per 100 g are treated for about 2 hours in a hollander. During this period 4 g of resin size, then 30 g of an approximately 15% strength pigment dispersion obtained by grinding 4.8 g of the pigment obtained according to Example 12 with 4.8 g of dinaphthylmethanedisulphonic acid and 22 g of water in a ball mill and then 5 g of aluminium sulphate are added at intervals of a quarter of an hour.

After finishing on the paper machine, an orange-coloured paper with outstanding fastness to light is obtained.

EXAMPLE 68

The orange pigmented paper prepared according to Example 67 is saturated with a 55% strength solution of a ureaformaldehyde resin in n-butanol and burnt-in at 140° C. An orange-coloured paper laminate with very good fastness to migration and outstanding fastness to light is obtained.

A paper laminate with identical fastness properties is obtained by laminating a paper which has been printed, by the gravure printing process, with a printing ink which contains the orange-coloured pigment fine paste indicated in Example 55 and water-soluble or saponifiable binders.

EXAMPLE 69

20 g of the pigment obtained according to Example 12 are pre-dispersed in 50 g of dimethylformamide using a dissolver and, with the addition of a dispersing auxiliary and of 50 g of a 10% strength solution of polyacrylonitrile in dimethylformamide, subjected to grinding in a bead mill. After separating off residual coarse particles, the pigment composition is added, in portions, according to known processes to a spinning solution of PAN and the mixture is homogenised and spun to filaments by a dry or wet spinning process which is known and customary in the art.

The colorations obtained in this way display very good brilliance and fastness to rubbing, migration, heat, light and weathering.

EXAMPLE 70

The compound of example 1 can further be prepared as follows: 300 g of malonic acid diethylester, 580 g of anthranilic acid amide and 6 g diazobicyclooctane are stirred for 5 hours in 1.2 l o-dichlorobenzene at 180° C. (temperature of the heating bath). Volatile reaction products are distilled off during heating. The precipitate is filtered off at 80° C., washed with methanol and dried at 80° C. in vacuo. 480 g (84% of theory) of the compound of the formula

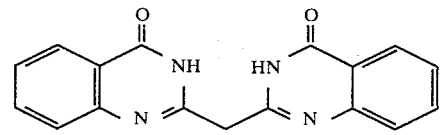

are obtained as a yellowish powder which does not melt on heating to 300° C. Elementary analysis shows good corresponding with the calculated figures.

EXAMPLE 71

The compound of example 12 can further be prepared as follows: 120 g of the coupling component obtained according to example 70 and 140 g 1-amino-5-benzoylaminoanthraquinone (87% pure) are stirred for 3 hours at 40° C. in a mixture consisting of 900 ml nitrobenzene and 200 ml 85% strength aqueous formic acid. Within 60 minutes a solution of 70 g sodium nitrite in 100 ml water is added dropwise. After removal of water in vacuo stirring is continued for 1 hour at 150° C. At 100° C. the precipitate is filtered off by suction, washed with nitrobenzene, methanol and water and dried. 215 g (92% of theory) of the pigment mentioned in example 12a are obtained.

We claim:

1. Azo pigment of the formula

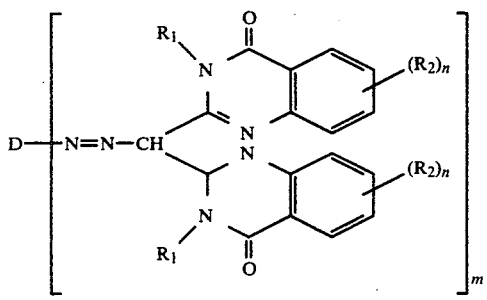

wherein
D is the radical of an aromatic or hetero-aromatic amine which is free from sulphonic acid groups;
m is the integer 1 or 2;
n denotes 0, 1, 2, 3 or 4;
$R_1$ is hydrogen or $C_1$–$C_4$ alkyl; and
$R_2$ is chlorine, bromine, $Cl_1$–$C_4$-alkyl, $C_1$–$C_4$-alkoxy, nitro, trifluoromethyl, cyano, carboxamide, $C_1$–$C_4$-alkyl-carboxamide, phenylcarboxamide, $C_1$–$C_4$ alkylphenylcarboxamide, $C_1$–$C_4$-alkoxyphenylcarboxamide, fluoro-, chloro-, bromo-phenylcarboxamide, nitrophenylcarboxamide, benzylcarboxamide, $C_1$–$C_4$-alkylbenzylcarboxamide, $C_1$–$C_4$-alkoxybenzylcarboxamide, fluoro-, chloro-, bromo-benzylcarboxamide, nitrobenzylcarboxamide, sulphonamide, $C_1$–$C_4$-alkylsulphonamide, phenylsulphonamide, $C_1$–$C_4$-alkylphenylsulphonamide, $C_1$–$C_4$-alkoxyphenylsulphonamide, fluoro-, chloro-, bromo-phenylsulphonamide, nitrophenylsulphonamide, benzylsulphonamide, $C_1$–$C_4$- alkylbenzylsulphonamide, $C_1$–$C_4$-alkoxybenzylsulphonamide, fluoro-, chloro-, bromo-benzyl sulphonamide, nitrobenzylsulphonamide, $C_1$–$C_4$-alkylcarbonylamino, benzoylamino, chlorobenzoylamino, $C_1$–$C_4$-alkylbenzoylamino, $C_1$–$C_4$-alkoxybenzoylamino, nitrobenzoylamino, phenylamino, $C_1$–$C_4$-alkylphenylamino, $C_1$–$C_4$-alkoxyphenylamino, fluoro-, chloro-, bromo-phenylamino, or nitrophenylamino.

2. Azo pigment according to claim 1 of the formula

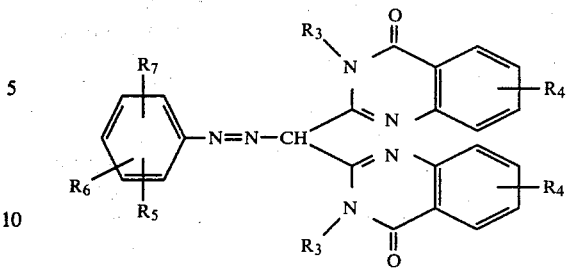

where
$R_3$ is hydrogen or methyl;
$R_4$ is hydrogen, $C_1$–$C_4$ alkyl, $C_1$–$C_4$-alkoxy, halogen, nitro, $C_1$–$C_4$-alkylcarbonylamino, or $C_1$–$C_4$-alkylsulphonylamino;
$R_5$ is hydrogen, halogen, $C_1$–$C_4$-alkyl, $C_1$–$C_4$-alkoxy, nitro, cyano, $C_1$–$C_4$-alkylsulphonyl, trifluoromethyl, carboxamide, $C_1$–$C_4$-alkylcarboxamide, phenylcarboxamide, $C_1$–$C_4$-alkylphenylcarboxamide, $C_1$–$C_4$-alkoxyphenylcarboxamide, fluoro-, chloro-, bromo-phenylcarboxamide, nitrophenylcarboxamide, benzylcarboxamide, $C_1$–$C_4$-alkylbenzylcarboxamide, $C_1$–$C_4$-alkoxybenzylcarboxamide, fluoro-, chloro-, bromo-benzylcarboxamide, nitrobenzylcarboxamide, sulphonamide, $C_1$–$C_4$-alkylsulphonamide, phenylsulphonamide, $C_1$–$C_4$-alkylphenylsulphonamide, $C_1$–$C_4$-alkoxyphenylsulphonamide, fluoro-, chloro-, bromo-phenylsulphonamide, nitrophenylsulphonamide, benzylsulphonamide, $C_1$–$C_4$-alkylbenzylsulphonamide, $C_1$–$C_4$-alkoxybenzylsulphonamide, fluoro-, chloro-, bromo-benzylsulphonamide, nitrobenzylsulphonamide, $C_1$–$C_4$-alkylcarbonylamino, benzoylamino, chlorobenzoylamino, $C_1$–$C_4$-alkylbenzoylamino, $C_1$–$C_4$ alkoxybenzoylamino, nitrobenzoylamino, $C_1$–$C_4$-alkoxycarbonyl;
$R_6$ is hydrogen, fluorine, chlorine, bromine, $C_1$–$C_4$-alkyl, cyano, $C_1$–$C_4$-alkoxy, nitro, or trifluoromethyl; and
$R_7$ is hydrogen, chloride, $C_1$–$C_4$-alkyl or $C_1$–$C_4$-alkoxy.

3. Azo pigment according to claim 1 of the formula

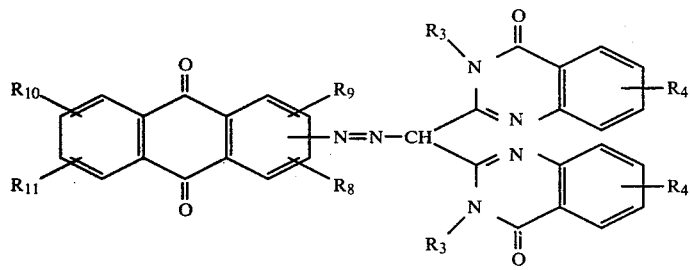

wherein
$R_3$ is hydrogen or methyl;
$R_4$ is hydrogen, $C_1$–$C_4$-alkyl, $C_1$–$C_4$-alkoxy, fluorine, chlorine, bromine, nitro, $C_1$–$C_4$-alkylcarbonylamino, or $C_1$–$C_4$-alkylsulphonylamino;
$R_8$ denotes hydrogen, fluroine, chlorine, bromine, nitro, $C_1$–$C_4$-alkyl, $C_1$–$C_4$-alkoxy, $C_1$–$C_4$-alkylamino, benzylamino, cyclohexylamino, $C_1$–$C_4$-alkylmercapto, phenylmercapto, $C_1$–$C_4$-alkylphenylmercapto, $C_1$–$C_4$-alkoxyphenylmercapto, fluoro-, chloro-, bromophenylmercapto, nitrophenylmercapto, carboxamide, mono- or di-$C_1$-$C_4$-alkylcarboxamide, mono- or diphenylcarboxamide, mono- or di- $C_1$-$C_4$-alkylphenylcarboxamide, mono- or di- $C_1$-$C_4$-alkoxyphenylcarboxamide, mono- or di-fluoro, chloro,bromophenylcarboxamide, mono- or di-nitrophenylcarboxamide, mono- or di-benzylcarboxamide, $C_1$-$C_4$-alkylcarbonylamino, benzoylamino, chlorobenzoylamino, $C_1$-$C_4$-alkylbenzoylamino, $C_1$-$C_4$-alkoxybenzoylamino, nitrobenzoylamino, bromobenzoylamino, phenylamino, $C_1$-$C_4$-alkylphenylamino, $C_1$-$C_4$-alkoxyphenylamino, chlorophenylamino, nitrophenylamino, $C_1$-$C_4$ alkylsulphonylamino, phenylsulphonylamino, $C_1$-$C_4$-alkylphenylsulphonylamino, $C_1$-$C_4$-alkoxyphenylphenylsulphonylamino, fluoro-, chloro-, bromophenylsulphonylamino, or nitrophenylsulphonylamino, $C_1$-$C_4$-alkylcarbonyl, $C_1$-$C_4$-alkoxycarbonyl;

$R_9$ is hydrogen, chlorine or hydroxyl;

$R_{10}$ is hydrogen halogen, fluorine, chlorine, bromine, nitro, $C_1$-$C_4$-alkyl, $C_1$-$C_4$-alkoxy, $C_1$-$C_4$-alkoxycarbonyl, $C_1$-$C_4$-alkylcarbonyl, benzylamino, cyclohexylamino, $C_1$-$C_4$-alkylmercapto, phenylmercapto, $C_1$-$C_4$-alkylphenylmercapto, $C_1$-$C_4$-alkoxyphenylmercapto, fluoro-, chloro-, bromophenylmercapto, nitrophenylmercapto, carboxyl, hydroxy, carboxamide, mono- or di- $C_1$-$C_4$-alkylcarboxamide, mono- or diphenylcarboxamide, mono- or di- $C_1$-$C_4$-alkylphenylcarboxamide, mono- or di- $C_1$-$C_4$-alkoxyphenylcarboxamide, mono- or di- fluoro-, chloro-, bromophenylcarboxamide, mono- or di- nitrophenyl carboxamide, mono- or di- benzylcarboxamide, $C_1$-$C_4$-alkylcarbonylamino, benzoylamino, chlorobenzoylamino, $C_1$-$C_4$-alkylbenzoylamino, $C_1$-$C_4$-alkoxybenzoylamino, nitrobenzoylamino, bromobenzoylamino, phenylamino, $C_1$-$C_4$-alkylphenylamino, $C_1$-$C_4$-alkoxyphenylamino, chlorophenylamino, bromophenylamino, nitrophenylamino, $C_1$-$C_4$-alkylsulphonylamino, phenylsulphonylamino, $C_1$-$C_4$-alkylphenylsulphonylamino, $C_1$-$C_4$-alkoxyphenylsulphonylamino, fluoro-, chloro-, bromo-phenylsulphonylamino, or nitrophenylsulphonylamino; and $R_{11}$ is hydrogen, fluorine, chlorine, bromine or hydroxyl.

4. Azo pigment according to claim 1 of the formula

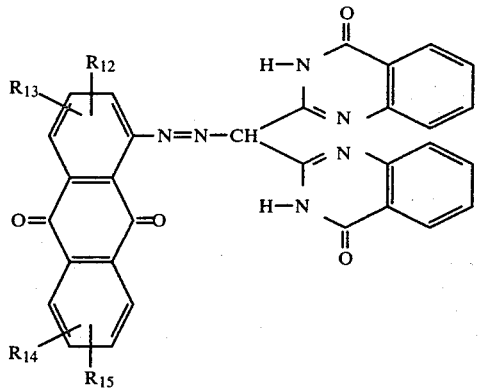

wherein
$R_{12}$, $R_{13}$, $R_{14}$ and $R_{15}$ are hydrogen, chlorine, bromine, carboxyl, $C_1$-$C_4$-alkoxycarbonyl, carboxamide, $C_1$-$C_4$-alkylcarbonylamino, benzoylamino, mono- or di-nitrobenzoylamino, benzoylamino substituted with 1–5 chlorines or bromines, $C_1$-$C_4$-alkylsulphonylamino, phenylsulphonylamino, methylphenylsulphonylamino, methoxysulphonylamino, or chlorophenylsulphonylamino.

* * * * *

UNITED STATES PATENT AND TRADEMARK OFFICE
CERTIFICATE OF CORRECTION

PATENT NO. : 4,225,489

DATED : September 30, 1980

INVENTOR(S) : MEINHARD ROLF; RUTGER NEEFF; WALTER MÜLLER

It is certified that error appears in the above—identified patent and that said Letters Patent is hereby corrected as shown below:

column 2, line 27, delete "a" after "and".

Signed and Sealed this

Seventeenth Day of March 1981

[SEAL]

Attest:

RENE D. TEGTMEYER

*Attesting Officer*     *Acting Commissioner of Patents and Trademarks*